United States Patent
Muto

(10) Patent No.: US 6,598,460 B2
(45) Date of Patent: Jul. 29, 2003

(54) EXPLOSION-PROOF APPARATUS AND GAS CHROMATOGRAPH FOR PROCESS

(75) Inventor: Hiroyuki Muto, Tokyo (JP)

(73) Assignee: Yamatake Corporation (JP)

( * ) Notice: Subject to any disclaimer, the term of this patent is extended or adjusted under 35 U.S.C. 154(b) by 60 days.

(21) Appl. No.: 09/773,718

(22) Filed: Jan. 31, 2001

(65) Prior Publication Data

US 2002/0043097 A1 Apr. 18, 2002

(30) Foreign Application Priority Data

Oct. 13, 2000 (JP) ........................... 2000-313560

(51) Int. Cl.$^7$ .................. G01N 30/02; G01N 30/90
(52) U.S. Cl. .................. 73/23.35; 73/23.4; 422/89; 96/101; 95/82
(58) Field of Search ................ 73/23.35, 23.39, 73/23.4, 23.41, 23.42; 422/89; 95/82; 96/101, 104, 106

(56) References Cited

U.S. PATENT DOCUMENTS 3,910,765 A * 10/1975 Tinklepaugh et al. ...... 73/23.25
4,006,624 A * 2/1977 Annino et al. ............. 73/23.35
4,059,994 A * 11/1977 Annino et al. ............. 73/23.25
4,088,458 A * 5/1978 Jourdan .................... 73/23.25
5,340,543 A * 8/1994 Annino et al. ............. 73/23.41
6,004,514 A * 12/1999 Hikosaka et al. .......... 73/23.42

FOREIGN PATENT DOCUMENTS

| JP | 4-259856 | 9/1992 |
| JP | 7-248320 | 9/1995 |

* cited by examiner

Primary Examiner—Daniel S. Larkin
(74) Attorney, Agent, or Firm—Blakely, Sokoloff, Taylor & Zafman

(57) ABSTRACT

An explosion-proof apparatus includes a pressure resistant explosion-proof case, heater, manifold, and analyzer unit. The heater is disposed in the pressure resistant explosion-proof case. The manifold is heated by the heater in the pressure resistant explosion-proof case and supplies heat from the heater to an outside of the pressure resistant explosion-proof case by heat conduction. The analyzer unit is disposed outside the pressure resistant explosion-proof case in contact with the manifold, and is heated by heat supplied from the manifold.

9 Claims, 7 Drawing Sheets

EXPLOSION-PROOF APPARATUS AND GAS CHROMATOGRAPH FOR PROCESS

BACKGROUND OF THE INVENTION

The present invention relates to various types of explosion-proof apparatuses installed in a petrochemical plant and the like, and more particularly to an explosion-proof apparatus with a heating means and heating target, and a gas chromatograph for a process.

Generally, in a petrochemical process or steel process, a gas chromatograph for a process has conventionally been used as an apparatus for analyzing the composition of a process gas, monitoring each process step on the basis of the analysis result, and performing various types of control operations.

In a gas chromatograph of this type, a measurement gas (sample gas) to be measured which is sampled from a process line is fed to a column by a carrier gas, and is separated into respective components in the column by utilizing the difference in moving speed based on differences in adsorptivity (affinity) or partition coefficient of the respective components with respect to a stationary phase. The separated gas components are detected by a thermal conductivity detector. The detection values are converted into electrical signals, and waveform-processed by a controller. Based on the waveform-processed signals, the composition of the measurement target gas is analyzed. The process is controlled based on the analytic values, and the chromatogram waveforms are recorded by a recorder.

A gas chromatograph has an analyzer unit with a valve for switching flow paths for the sample gas and carrier gas, a column for separating the sample gas into the respective gas components, a detector for detecting the gas components, and the like, an electrical apparatus portion for driving and controlling the gas chromatograph, and the like. In the analysis of the sample gas, when the temperatures of the column flow path selector valve, sample gas, detector, and the like fluctuate (decrease), the gas components (heavy components) are condensed, and the concentrations of the components do not match the original sample concentrations. Hence, in order to guarantee correct measurement, a heating means for heating the analyzer unit and a thermostatic chamber for keeping the temperature of the analyzer unit are provided.

When a gas chromatograph of this type is installed in a petrochemical plant or the like, if a combustible gas enters the gas chromatograph to come into contact with an electrical circuit portion, it may explode. For this reason, the gas chromatograph must have a predetermined explosion-proof structure in the same manner as various types of electrical meters.

Japanese Patent Laid-Open Nos. 4-248320 and 4-259856 disclose a chromatograph in which a thermostatic chamber is disposed in a pressure resistant explosion-proof case and an analyzer unit and heating means are built into the thermostatic chamber. In this arrangement, the heating means and thermostatic chamber keep the column and flow path control valve to a temperature optimum for separating and analyzing the sample gas.

When the analyzer unit is disposed in the thermostatic chamber in this manner to control the sample gas and carrier gas to a predetermined temperature, the thermal conductivity of the gas can be measured at high precision. Since the heating means to which a voltage that can generate electric spark is disposed in the pressure resistant explosion-proof chamber, even if explosion occurs in the case, the flame is prevented from leaking outside.

In the conventional gas chromatograph, since the thermostatic chamber is built into the pressure resistant explosion-proof case and the analyzer unit and heating means are disposed in the thermostatic chamber, the internal volume of the pressure resistant explosion-proof case increases, and the outer size of the pressure resistant explosion-proof case also increases accordingly. When the internal volume of the pressure resistant explosion-proof case increases, when an explosion occurs, the explosive pressure generated in the pressure resistant explosion-proof case increases, and the flame tends to leak outside. In order to reliably prevent flame leakage to the outside, a long explosion-proof spacing must be formed, and at least the wall thickness defining the explosion-proof spacing must be increased. As a result, in the conventional gas chromatograph, size, weight, and cost reductions are limited.

This problem arises not only in a gas chromatograph for a process, but is common among various types of explosion-proof apparatuses in general each installed in a petrochemical plant or the like and having in it a heating target and a heating means for the heating target.

SUMMARY OF THE INVENTION

It is an object of the present invention to provide an explosion-proof apparatus in which the size, weight, and cost of its pressure resistant explosion-proof case can be reduced, and a gas chromatograph for a process.

In order to achieve the above object, according to the present invention, there is provided an explosion-proof apparatus comprising a pressure resistant explosion-proof case, heating means disposed in the pressure resistant explosion-proof case, a heat conduction member heated by the heating means in the pressure resistant explosion-proof case and adapted to supply heat from the heating means to an outside of the pressure resistant explosion-proof case by heat conduction, and a heating target disposed outside the pressure resistant explosion-proof case in contact with the heat conduction member and heated by heat supplied from the heat conduction member.

DESCRIPTION OF THE PREFERRED EMBODIMENT

The present invention will be described in detail with reference to the accompanying drawings.

Figure 1:
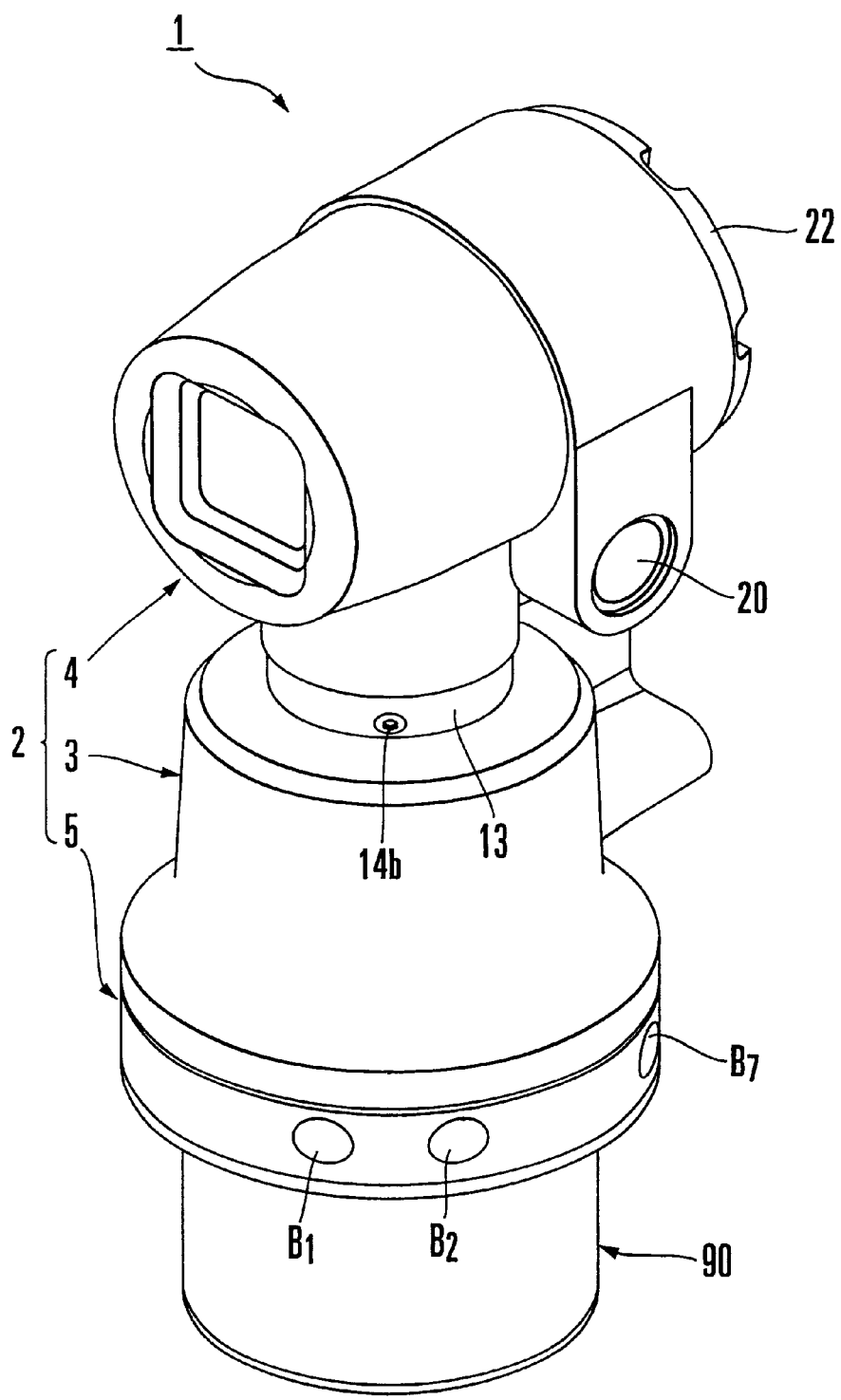
FIG. 1 is a perspective view showing the outer appearance of a gas chromatograph for a process according to an embodiment of the present invention.

FIGS. 1 to 10 show a gas chromatograph for a process according to an embodiment of the present invention. Referring to FIG. 1, a gas chromatograph 1 has a pressure resistant explosion-proof case 2 covering the entire arrangement. The pressure resistant explosion-proof case 2 is comprised of a housing 3 for accommodating the main body portion of the gas chromatograph 1, a terminal case 4 mounted on the upper side of the housing 3, and a manifold 5 mounted on the lower side of the housing 3. An explosion-proof area 6 is formed in the pressure resistant explosion-proof case 2.

Figure 2:
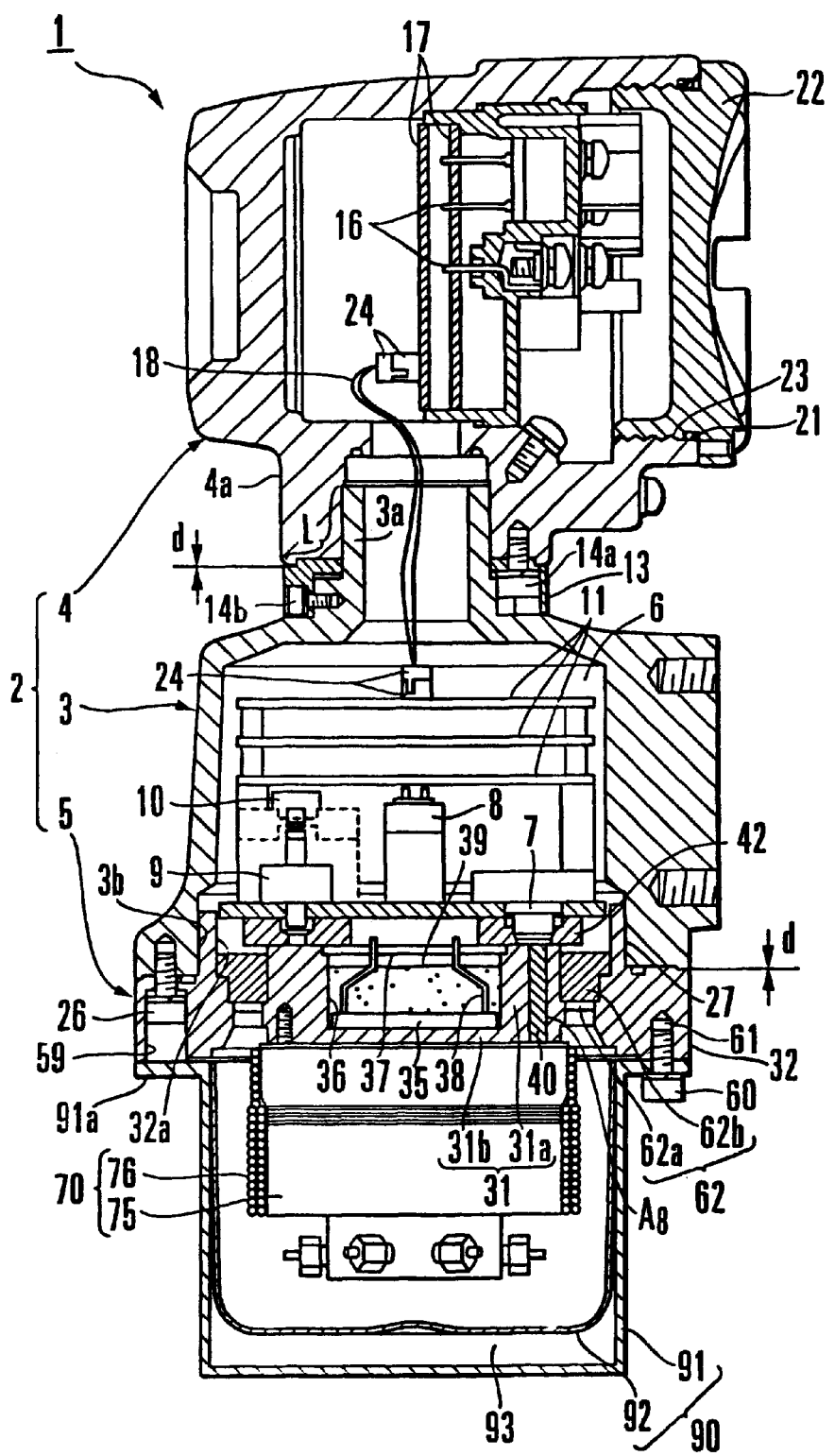
FIG. 2 is a sectional view of the gas chromatograph shown in FIG. 1.
Figure 3:
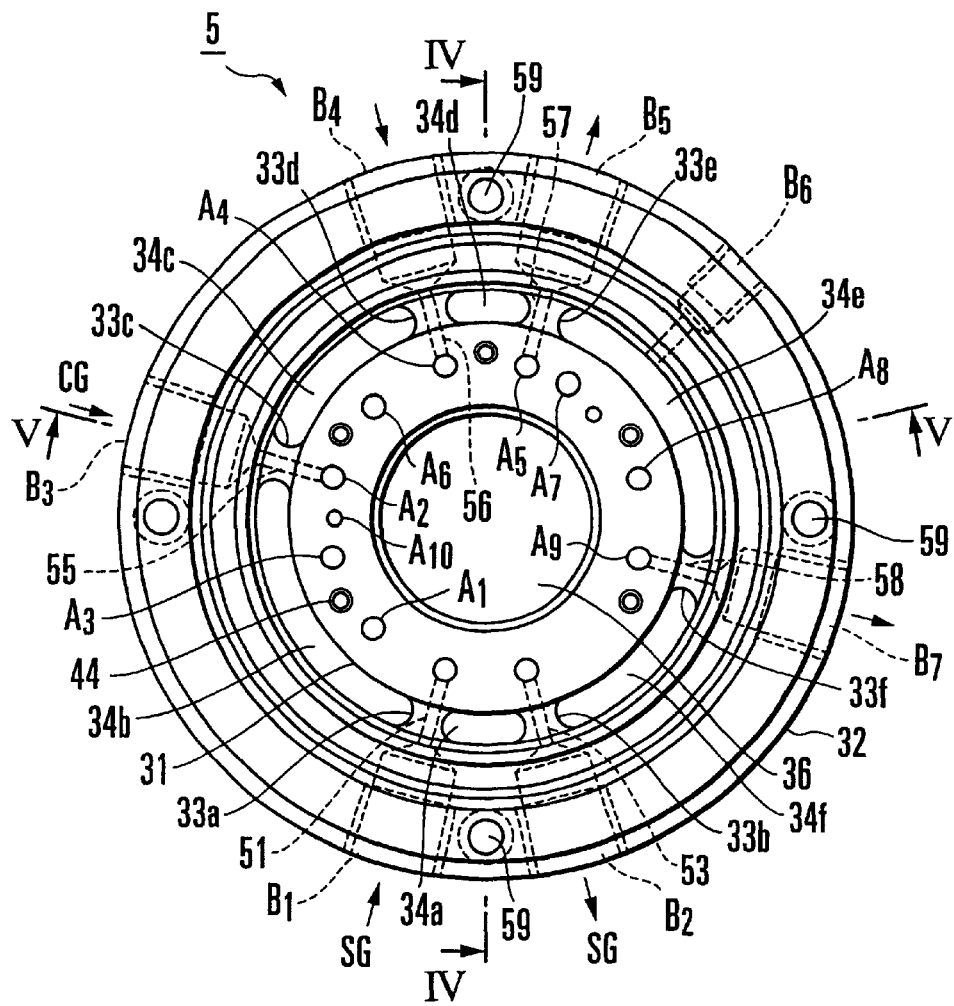
FIG. 3 is a plan view of the manifold shown in FIGS. 1 and 2.
Figure 4:
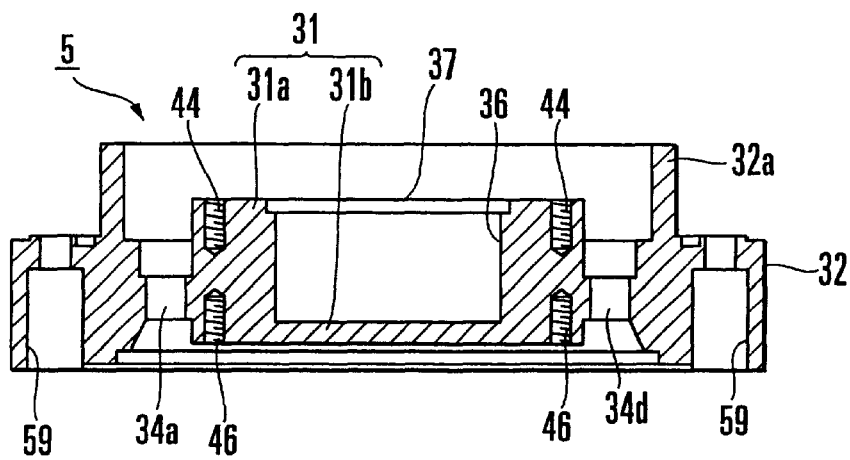
FIG. 4 is a sectional view taken along the line IV—IV of FIG. 3.
Figure 5:
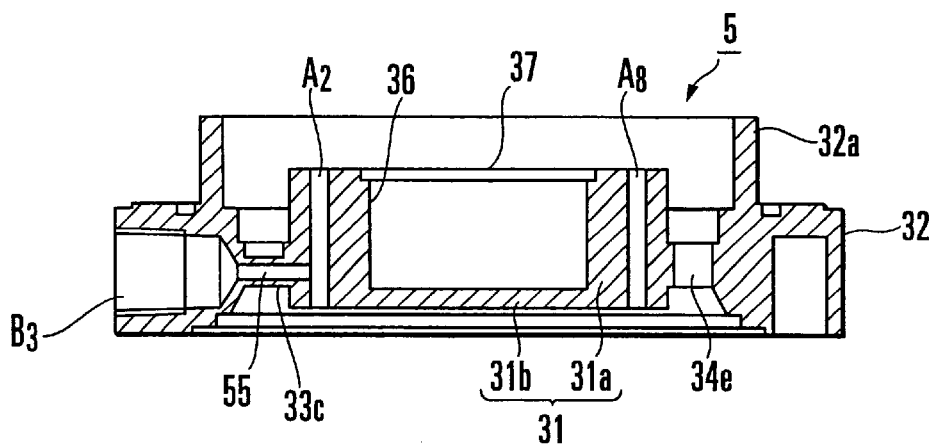
FIG. 5 is a sectional view taken along the line V—V of FIG. 3.
Figure 6:
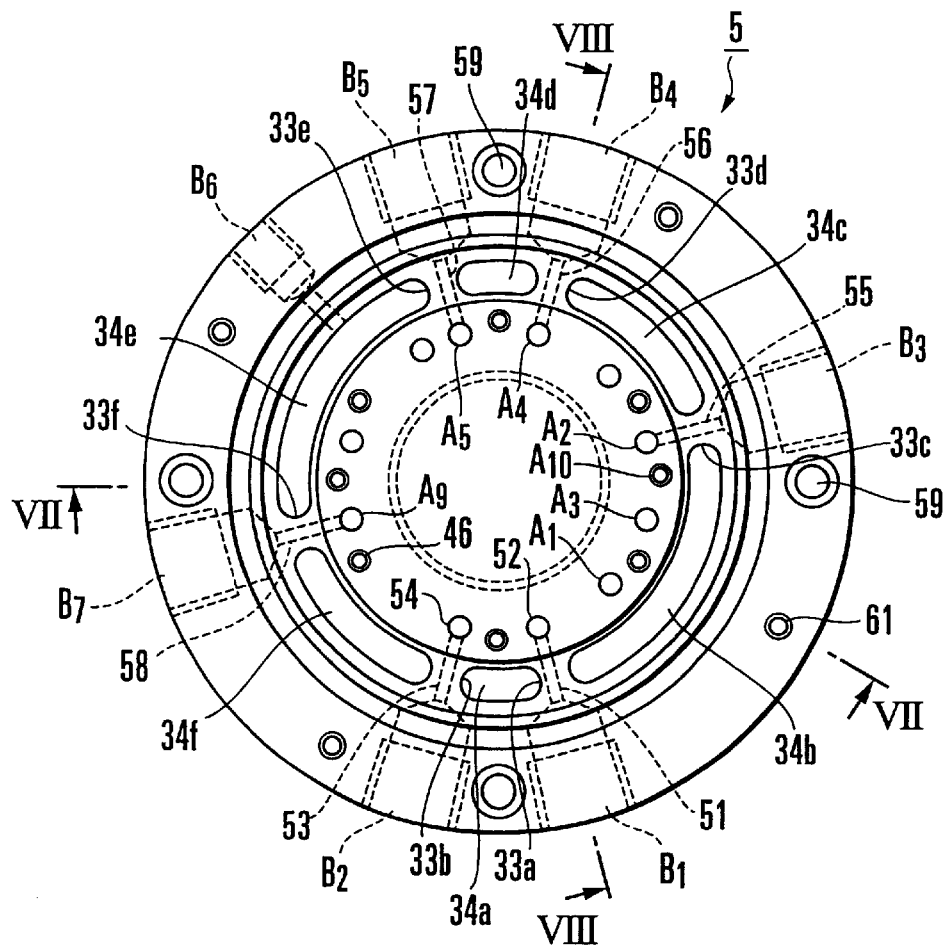
FIG. 6 is a bottom view of the manifold shown in FIGS. 1 and 2.
Figure 7:
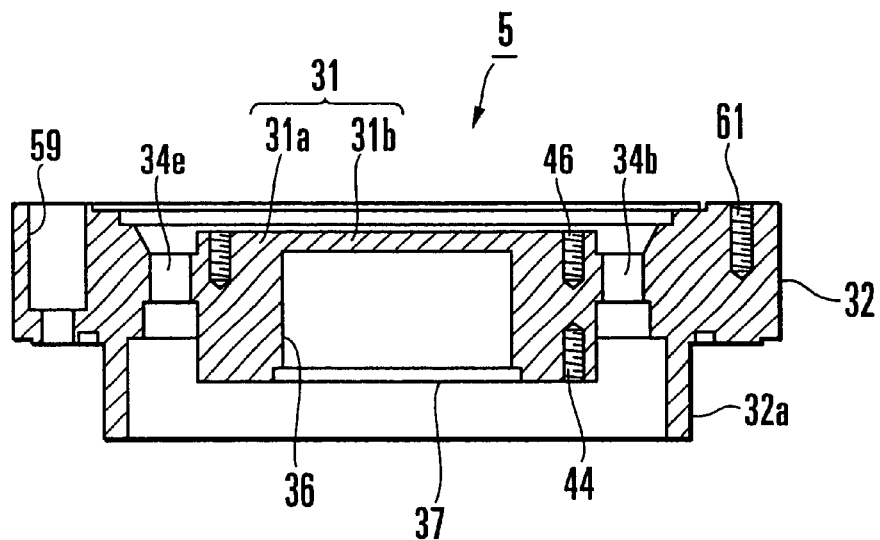
FIG. 7 is a sectional view taken along the line VII—VII of FIG. 6.

The housing 3 is formed into a cylindrical body from a metal, such as aluminum, and is fixed to a stanchion (not shown) through a bracket. The housing 3 accommodates a detector 7, solenoid valve 8, microvalve 9, pressure sensor 10, a plurality of printed circuit boards 11, and the like, as shown in FIG. 2. A connecting portion 3a formed of a small-diameter cylindrical portion integrally projects from the center of the upper surface of the housing 3, and the terminal case 4 is attached to the connecting portion 3a.

The detector 7, solenoid valve 8, microvalve 9, and pressure sensor 10 are electrically connected to a control circuit 12 (FIG. 10) mounted on the printed circuit board 11. As the detector 7, a thermal conductivity detector (TCD) is used, and its detection signal is sent to the control circuit 12 and is waveform-processed. The pressure sensor 10 detects the pressure of a carrier gas CG and outputs a detection signal to the control circuit 12. The control circuit 12 controls the microvalve 9 on the basis of the detection signal from the pressure sensor 10, to adjust the pressure of the carrier gas CG.

The terminal case 4 has an open rear surface and is formed into a cylindrical body with an axis perpendicular to the housing 3. A cylindrical connecting portion 4a vertically hangs integrally from the lower portion of the terminal case 4. A neck holder 13 formed of a ring with an inverted L-shaped section is fixed to the lower end face of the connecting portion 4a with a plurality of bolts 14a. The connecting portion 4a fits on the outer surface of the connecting portion 3a of the housing 3. In this fitting state, the neck holder 13 is fixed to the connecting portion 3a with a plurality of bolts 14b.

An explosion-proof spacing with a predetermined gap d and depth L is defined by the connecting portion 3a of the housing 3, the connecting portion 4a of the terminal case 4, and the neck holder 13 to prevent leakage of the flame to the outside. For example, the gap d and depth L of the explosion-proof spacing are set to satisfy d=0.15 mm or less and L=12.5 mm or more when the volume of the pressure resistant explosion-proof case 2 is 2,000 cc or less and the joint is a spigot joint.

A plurality of terminals 16 and printed circuit boards 17 to be connected to external wires are disposed in the terminal case 4. The terminals 16 are connected to the electrical circuits of the printed circuit boards 17. The printed circuit boards 17 are electrically connected to the control circuit 12 (FIG. 10) mounted on the printed circuit board 11 in the housing 3 through cords 18.

A connecting portion 20 (FIG. 1), to which a conduit of an external wire (not shown) is to be connected by insertion while keeping an explosion-proof spacing with a predetermined gap and depth, is formed on the outer surface of the terminal case 4. A rear opening 21 of the terminal case 4 is closed with a terminal cover 22 by threadable engagement. A threaded joint portion 23 of the terminal cover 22 and rear opening 21 also defines an explosion-proof spacing with a predetermined gap and depth. The gap and depth of the explosion-proof spacing formed at the threaded joint portion 23 are defined by the number of threads. Reference numeral 24 denotes a connector.

The disk-like manifold 5 is fabricated from a metal material, such as stainless steel, and is fitted in a lower opening 3b of the housing 3 and fixed to it with a plurality of bolts 26. A joint 27 of the housing 3 and manifold 5 also defines an explosion-proof spacing with the predetermined gap d and depth L.

As shown in FIGS. 3 to 8, the manifold 5 is comprised of a heat receiving portion 31, a ring portion 32 surrounding the heat receiving portion 31, and six connecting portions 33a to 33f that connect the ring portion 32 and heat receiving portion 31. Six arcuate punched portions 34a to 34f for separating the connecting portions 33a to 33f are formed between the heat receiving portion 31 and ring portion 32.

The heat receiving portion 31 is comprised of a thick-walled cylindrical portion 31a and a thin-walled bottom plate portion 31b which closes the lower surface of the cylindrical portion 31a, to have a cup shape, and forms an accommodating portion 36 for accommodating a heater 35 (FIGS. 2 and 10) serving as a heating means. The heater 35 is electrically connected to a printed circuit board 37 through wires 38, and heats the heat receiving portion 31 to a predetermined temperature (about 90° C. to 100° C.) upon being energized. The printed circuit board 37 is attached to cover an opening in the upper surface of the heat receiving portion 31, and is electrically connected to the control circuit 12. After being accommodated in the accommodating portion 36, the heater 35 may be molded with a synthetic resin 39 to improve heat conduction to the heat receiving portion 31.

Figure 9:
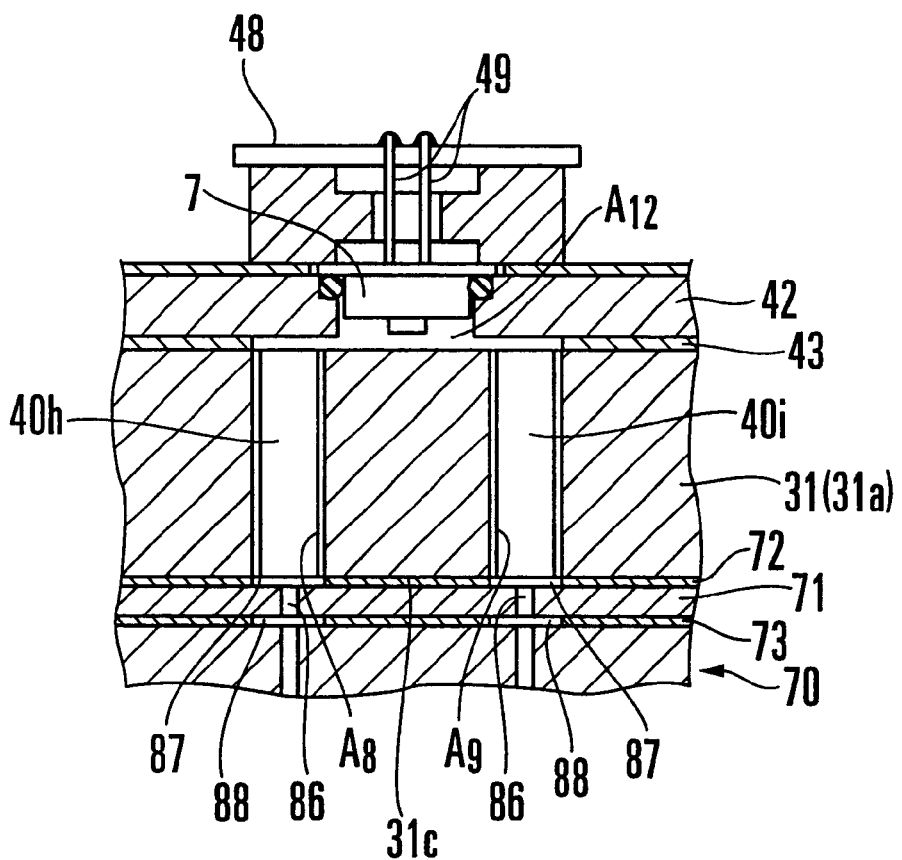
FIG. 9 is a sectional view of the detector portion shown in FIG. 2.

Nine gas flow paths A1 to A9 formed of axial through holes are formed in the cylindrical portion 31a of the heat receiving portion 31 to separate from each other in the circumferential direction. As shown in FIG. 9, frame arresters 40a to 40i made of a metal are fitted in the gas flow paths A1 to A9. The frame arresters 40 and the gas flow paths A1 to A9 define an explosion-proof spacing with a predetermined gap (d=0.15 mm) and depth (L=20 mm).

Figure 10:
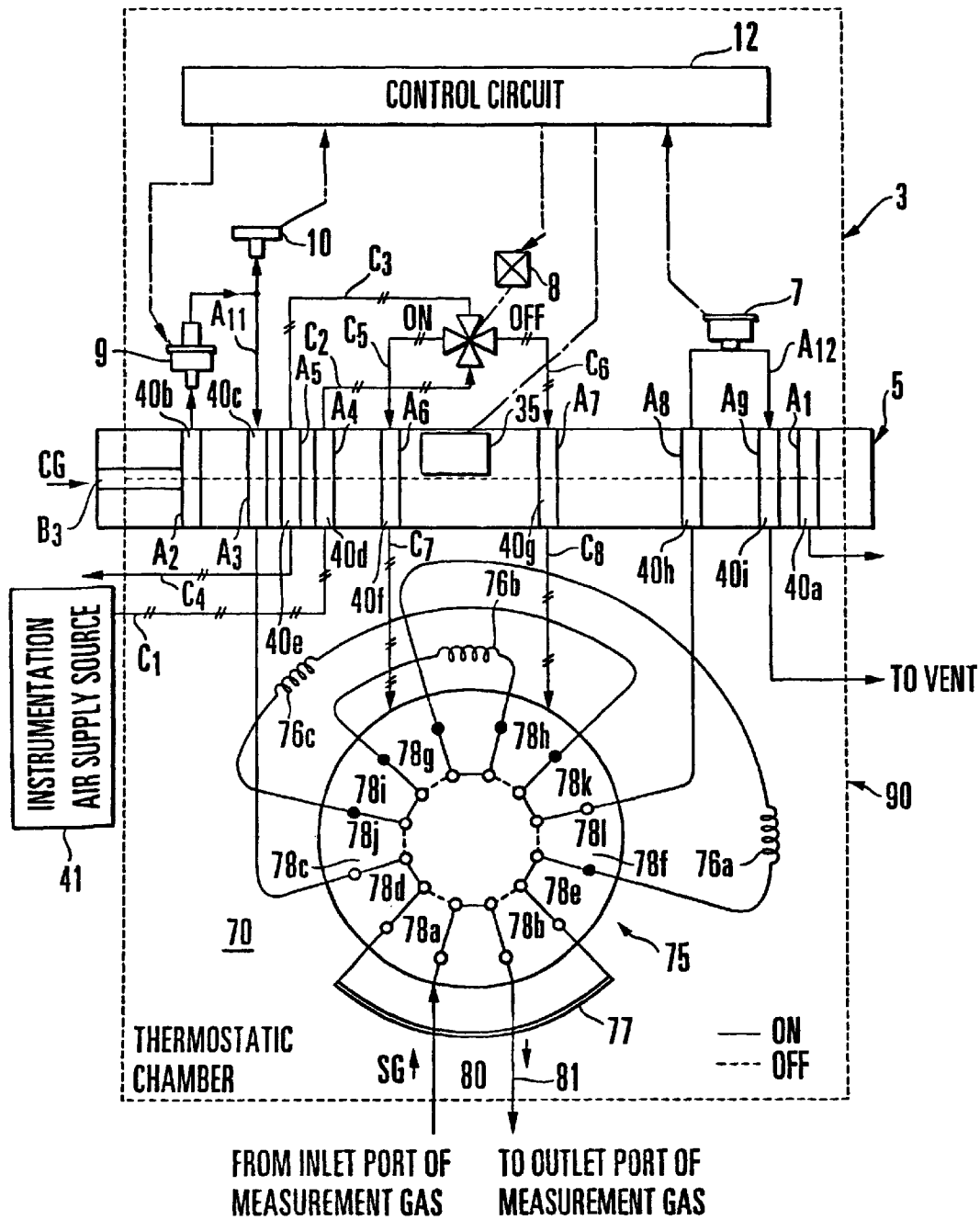
FIG. 10 is a system configuration view showing the flow path system and control system of the gas chromatograph shown in FIGS. 1 and 2.

The gas flow path A1 forms a breather flow path for preventing a rise in internal pressure of the pressure resistant explosion-proof case 2. The gas flow paths A2 and A3 form carrier gas flow paths, and communicate with each other through a flow path A11, as shown in FIG. 10. The microvalve 9 and pressure sensor 10 are disposed in the flow path A11. The gas flow path A4 forms an instrumentation air inlet path, and has a lower opening connected to an instrumentation air supply source 41 through an air flow path C1 and an upper opening connected to the solenoid valve 8 through an air flow path C2.

The gas flow path A5 forms an instrumentation air discharge path, and has an upper opening connected to the solenoid valve 8 through an air flow path C3 and a lower opening connected to a vent air flow path C4. The gas flow paths A6 and A7 form instrumentation air paths, and have upper openings connected to the solenoid valve 8 through air flow paths C5 and C6 and lower openings connected to a flow path selector valve 75 (to be described later) through air flow paths C7 and C8. The gas paths A8 and A9 form a measurement gas inlet path and measurement gas discharge path, respectively, and communicate with each other through a flow path A12.

As shown in FIG. 9, a manifold plate 42 is fixed to the upper surface of the cylindrical portion 31a through a packing 43. A plurality of screw holes 44 (FIGS. 3 and 4), in which set screws (not shown) for fixing the manifold plate 42 are to be screwed, are formed in the upper surface of the cylindrical portion 31a. The detector 7 is disposed at a predetermined portion of the manifold plate 42 to face the flow path A12. The detector 7 is electrically connected to a printed circuit board 48 through lead wires 49. A plurality of flow paths including the flow paths A11 and A12 and respectively communicating with the gas flow paths A1 to A9 are formed between the packing 43 and the upper surface of the cylindrical portion 31a. A plurality of screw holes 46 (FIG. 4), in which set screws (not shown) for fixing an analyzer unit 70 (to be described later) are to be screwed, are formed in the lower surface of the cylindrical portion 31a.

Figure 8:
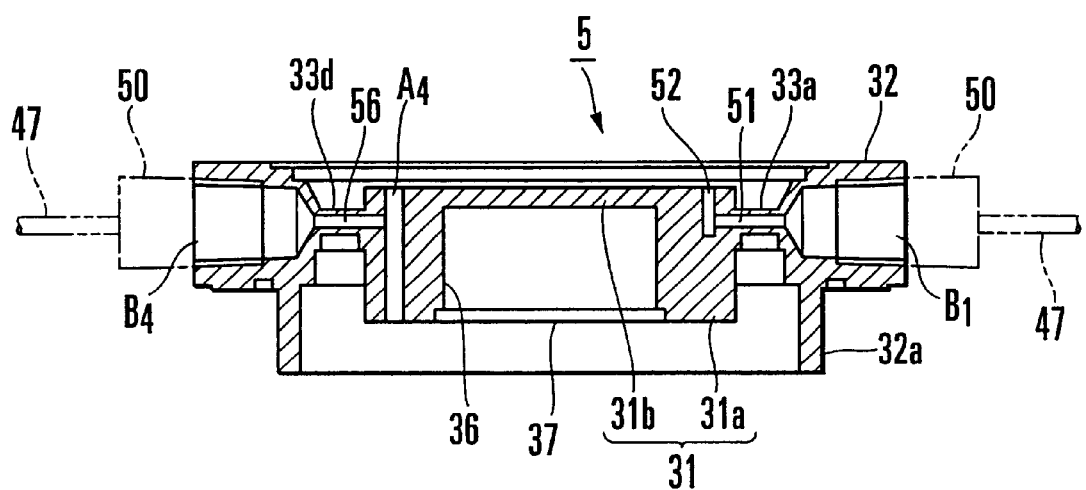
FIG. 8 is a sectional view taken along the line VIII—VIII of FIG. 6.

The ring portion 32 of the manifold 5 has a cylindrical portion 32a projecting from near the inner periphery of its upper portion integrally to fit in the lower opening 3b of the housing 3, and is fixed to the lower portion of the housing 3 with the bolts 26 (FIG. 2). The ring portion 32 has seven gas connection ports B1 to B7 (FIGS. 3 and 6) extending radially (in the radial direction) to open in the outer circumferential surface of the ring portion 32 separately from each other in the circumferential direction. As shown in FIG. 8, the gas connection ports B1 to B7 are connected to pipes 47 through appropriate pipe connecting tools 50.

The gas connection port B1 forms a sample gas inlet port, the gas connection port B2 forms a sample gas discharge port, and the gas connection port B3 forms a carrier gas inlet port. The gas connection port B4 forms an instrumentation air inlet port, the gas connection port B5 forms an instrumentation air discharge port, the gas connection port B6 forms a breather port, and the gas connection port B7 forms a measurement gas discharge port for discharging the detected sample gas to the outside.

The gas connection ports B3, B4, B5, and B7 respectively correspond to the gas flow paths A2, A4, A5, and A9, while the gas connection ports B1, B2, B3, B4, B5, and B7 respectively correspond to the connecting portions 33a to 33f. The breather port B6 is open to the punched portion 34e with an inner end formed of an annular groove.

A communication path 51 with one end communicating with the sample gas inlet port B1 and the other end communicating with a path 52 (FIGS. 6 and 8) formed of a blind hole in the lower surface of the cylindrical portion 31a is defined in the connecting portion 33a. A communication path 53 with one end communicating with the sample gas discharge port B2 and the other end communicating with a path 54 (FIG. 6) formed of a blind hole in the lower surface of the cylindrical portion 31a is defined in the connecting portion 33b. A communicating path 55 (FIGS. 3 and 5) through which the carrier gas flow path A2 and inlet port B3 communicate with each other is defined in the connecting portion 33c. A communication path 56 (FIG. 3) through which the instrumentation air inlet path A4 and port B4 communicate with each other is defined in the connecting portion 33d. A communication path 57 through which the instrumentation air inlet path A5 and port B5 communicate with each other is defined in the connecting portion 33e. A communication path 58 through which the measurement gas discharge path A9 and port B7 communicate with each other is defined in the connecting portion 33e.

A plurality of bolt attaching holes 59 (FIG. 4) in which the bolts 26 are to be attached extend through the ring portion 32, and a plurality of screw holes 61 (FIG. 7) in which bolts 60 (FIG. 2) for fixing a temperature keeping means 90 (to be described later) are to be screwed are formed in the lower surface of the ring portion 32.

A thermal insulator 62 is disposed in the gap between the heat receiving portion 31 and ring portion 32 so as to satisfy a predetermined explosion-proof standard. The thermal insulator 62 is comprised of a ring-like silicone rubber member 62a covering the punched portions 34e to 34f and supported by the connecting portions 33a to 33f, and a silicone resin member 62b filling the space surrounded by the upper surface of the silicone rubber member 62a, the heat receiving portion 31, and the ring portion 32. When the heater 35 heats the heat receiving portion 31, the thermal insulator 62 blocks heat conduction from the heat receiving portion 31 to the ring portion 32.

The analyzer unit 70 is attached to a lower surface (heat supply surface) 31c of the heat receiving portion 31 through a center plate 71 (FIG. 9). Packings 72 and 73 are respectively interposed between the heat receiving portion 31 and center plate 71, and between the center plate 71 and analyzer unit 70. As shown in FIGS. 2 and 10, the analyzer unit 70 is comprised of a flow path selector valve 75 and a column 76 wound around the flow path selector valve 75.

The flow path selector valve 75 has a metering pipe 77 and flow paths 78a to 78l for a sample gas SG and the carrier gas CG. The flow path selector valve 75 guides the sample gas SG, together with the carrier gas CG, to the detector 7 through the column 76 in measurement, and guides the carrier gas CG to the column 76 and detector 7 in non-measurement. As the flow path selector valve 75, a conventionally known pneumatically driven diaphragm valve, which is turned on/off by instrumentation air, is used, and is connected to the detector 7 through the air flow paths C7 and C8. The flow path 78a is connected to a supply pipe 80 for the sample gas SG, and the flow path 78b is connected to a sample gas sample gas discharge pipe 81. The flow path 78c is connected to the carrier gas flow path A3, and the flow path 78l is connected to the measurement gas inlet path A8.

When the flow path selector valve 75 is ON, it connects the flow paths 78a and 78b, the flow paths 78c and 78d, the flow paths 78e and 78f, the flow paths 78i and 78j, the flow paths 78g and 78h, and the flow paths 78k and 78l, as indicated by solid lines in FIG. 10. When the flow path selector valve 75 is OFF, it connects the flow paths 78a and 78d, the flow paths 78b and 78e, the flow paths 78c and 78j, the flow paths 78j and 78g, the flow paths 78h and 78k, and the flow paths 78f and 78l, as indicated by broken lines in FIG. 10.

The column 76 is comprised of first to third series-connected columns 76a to 76c. Powder such as activated carbon, activated alumina, molecular sieves, or the like appropriate for separating the components of the sample gas SG and having a uniform particle size fills the column 76 as the stationary phase. The first column 76a is connected between the flow paths 78f and 78g. The second column 76b is connected between the flow paths 78i and 78h. The third column 76c is connected between the flow paths 78j and 78k.

When the flow path selector valve 75 is ON, the sample gas SG supplied from the supplying pipe 80 is discharged outside via the flow path 78a-flow path 78b-sample gas discharge pipe 81. When the flow path selector valve 75 is OFF, the sample gas SG is discharged outside via the flow path 78a-flow path 78d-metering pipe 77-flow path 78e-flow path 78b-sample gas discharge pipe 81.

When the flow path selector valve 75 is ON, the carrier gas CG supplied from the carrier gas inlet port B3 is discharged outside the gas chromatograph via the carrier gas flow path A2-flow path A11-microvalve 9-pressure sensor 10-carrier gas flow path A3-flow path 78c-flow path 78d-metering pipe 77-flow path 78e-flow path 78f-first column 76a-flow path 78g-flow path 78h-second column 76b-flow path 78i-flow path 78j-third column 76c-flow path 78k-flow path 78l-measurement gas inlet path A8-flow path A12-detector 7-measurement gas discharge path A9.

When the flow path selector valve 75 is OFF, the carrier gas CG is discharged outside the gas chromatograph via the carrier gas flow path A2-flow path A11-microvalve 9-pressure sensor 10-carrier gas flow path A3-flow path 78c-flow path 78j-third column 76c-flow path 78k-flow path 78h-second column 76b-flow path 78i-flow path 78g-first column 76a-flow path 78f-flow path 78l-measurement gas inlet path A8-flow path A12-detector 7-measurement gas discharge path A9.

As shown in FIG. 9, paths 86, 87, and 88, which can connect the gas flow paths A3, A6, A7, and A8 and the flow path selector valve 75 to each other, the flow paths 78a and 78b and the supply pipe 80/sample gas discharge pipe 81 to each other, and the metering pipe 77 and the flow paths 78d and 78e to each other and are comprised of a plurality of holes, are formed in the center plate 71 and the packing 72 and 73, respectively.

A thermostatic chamber 90 serving as a temperature keeping means for keeping the temperature of the analyzer unit 70 by blocking it from the outer air is disposed under the ring portion 32 of the manifold 5, as shown in FIG. 2. The thermostatic chamber 90 is comprised of a bottomed cylindrical outer tube 91 made of stainless steel or the like, and an inner tube 92 accommodated in the outer tube 91. A flange 91a is integrally formed at the upper opening of the outer tube 91 to come into tight contact with the lower surface of the ring portion 32, and is fixed to the ring portion 32 with the bolts 60. The inner tube 92 is fixed to the inner surface of the upper end side of the outer tube 91 at its upper opening by welding or the like. A hollow portion 93 between the outer and inner tubes 91 and 92 forms a heat-insulated space held at substantially vacuum, so it suppresses adverse influence of a change in outer temperature to the analyzer unit 70.

With this arrangement, when the heat receiving portion 31 of the manifold 5 is heated by the heater 35, heat conducted from the heat receiving portion 31 is supplied from the heat supply surface 31c to the analyzer unit 70 accommodated in the thermostatic chamber 90 through the packing 72, center plate 71, and packing 73. The analyzer unit 70, having received heat from the heat receiving portion 31, is held at a predetermined temperature (e.g., 50° C.) in the thermostatic chamber means 90.

The operation of the gas chromatograph 1 with the above structure will be described with reference to FIG. 10.

When the flow path selector valve 75 is OFF (non-measurement state), its flow paths 78a to 78l are held at the state indicated by the broken lines. In this state, the sample gas SG supplied from the supply pipe 80 to the flow path 78a is discharged outside the gas chromatograph 1 via the flow path 78d-metering pipe 77-flow path 78e-flow path 78b-sample gas discharge pipe 81.

At this time, the carrier gas CG consisting of a pure gas, such as helium (He), nitrogen (N₂), hydrogen (H₂), or the like, supplied from the carrier gas inlet port B3 is discharged outside the gas chromatograph 1 via the carrier gas flow path A2-flow path A11-microvalve 9-pressure sensor 10-carrier gas flow path A3-flow path 78c-flow path 78j-third column 76c-flow path 78k-flow path 78h-second column 76b-flow path 78i-flow path 78g-first column 76a-flow path 78f-flow path 78l-measurement gas inlet path A8-flow path A12-detector 7-measurement gas flow path A9.

In measurement, the flow path selector valve 75 is turned on to switch the flow paths 78a to 78l from the state indicated by the broken lines to the state indicated by the solid lines, so the flow paths 78a and 78b communicate with each other and the flow paths 78d and 78e communicate with the metering pipe 77. Therefore, the sample gas SG metered and dispensed by the metering pipe 77 is fed out by the carrier gas CG guided to the metering pipe 77 via the carrier gas flow path A2-flow path A11-microvalve 9-pressure sensor 10-carrier gas flow path A3-flow path 78c-flow path 78d, and fed into the first column 76a via the flow path 78e-flow path 78f.

The sample gas SG fed into the first column 76a is roughly separated into a low-quality component group and a high-quality component group by a stationary phase filled in the first column 76a. The separated low- and high-quality components flow through the flow path 78g-flow path 78h-second column 76b-flow path 78i-flow path 78j-third column 76c, so they are further separated into respective components by the second and third columns 76b and 76c. The gas components respectively separated by the second and third columns 76b and 76c are fed to the flow path 78k-flow path 78l-measurement gas inlet path A8-flow path A12 and detected by the detector 7 in units of components. The detection signals are converted into electrical signals. The converted electrical signals are proportional to the concentrations of the respective gas components. Thus, process control and chromatogram waveform recording are performed on the basis of the signals waveform-processed by the control circuit 12.

When measurement is ended, the flow path selector valve 75 is turned off to the initial state, and the detector 7 and the first to third columns 76a to 76c are cleaned with the carrier gas CG.

In this embodiment, the heater 35 is arranged in the manifold 5 which forms the pressure resistant explosion-proof case 2 together with the housing 3, and the analyzer unit 70 is disposed outside the manifold 5 together with the thermostatic chamber 90. The analyzer unit 70 is heated to a predetermined temperature by heat conduction through the heat receiving portion 31 heated by the heater 35. According to this arrangement, the analyzer unit 70 need not be disposed in the pressure resistant explosion-proof case 2, and the pressure resistant explosion-proof case 2, particularly the housing 3, can be made compact and lightweight. Since the analyzer unit 70 is disposed in the thermostatic chamber 90, it is not adversely influenced by an external temperature change, and is set and held under an optimum temperature condition. As a result, measurement precision can be improved.

Since the gas connection ports B1 to B7 are radially formed in the ring portion 32 of the manifold 5, the pipe connecting tools 50 of the adjacent pipes 47 can be attached and detached more easily than in a case wherein the gas connection ports B1 to B7 are formed in the lower surface of the manifold 5. More specifically, since the gas connection ports B1 to B7 are radially formed in the outer circumferential surface of the ring portion 32, the farther from the center of the manifold 5, the larger the distance between the adjacent pipe connecting tools 50. Therefore, when the pipe connecting tools 50 are to be attached and detached with a tool such as a wrench, the tool less interferes with the adjacent pipe connecting tools 50, and the pipe connecting tools 50 can be attached and detached easily.

Since the communication paths 55, 56, 57, and 58 for connecting the gas flow paths A2, A4, A5, and A9 and the gas connection ports B3, B4, B5, and B7 to each other are formed in the connecting portions 33c, 33d, 33e, and 33f of the manifold 5, the gas flow paths A2, A4, A5, and A9 and the gas connection ports B3, B4, B5, and B7 need not be connected to each other through separate members such as pipes. Also, the temperatures of the communication paths 55, 56, 57, and 58 can be set substantially equal to the internal temperatures of the connecting portions 33c, 33d, 33e, and 33f. As a result, the temperature fluctuation of the gas can be decreased, and the sectional areas of the connecting portions can be decreased, so that the heat insulating effect can be enhanced.

The embodiment described above exemplifies a gas chromatograph for a process. However, the present invention is not limited to this at all, but can be applied to an explosion-proof apparatus with a heating means and its heating target. The column is made up of three columns, i.e., the first to third columns 76a to 76c. However, the present invention is not limited to this, and depending on the measurement gas, two columns may be used.

In the above embodiment, the gap d and depth L of the explosion-proof spacing can be any values if the flame will not leak outside, and are selected from the measurement values or explosion-proof standard values.

As has been described above, according to the present invention, the heating target is disposed outside the pressure resistant explosion-proof case so that it is heated by heat conduction through the pressure resistant explosion-proof case. Hence, the pressure resistant explosion-proof case can be made compact and lightweight to reduce the manufacturing cost of the apparatus.

Since the analyzer unit is disposed outside the manifold together with the heat keeping means and is heated by heat conduction through the manifold, the size, reduction, and cost of the pressure resistant explosion-proof case can be reduced.

Since the thermal insulator based on the explosion-proof standard is interposed in the gap between the heat receiving portion and ring portion, even if an explosion occurs in the pressure resistant explosion-proof case, the flame can be prevented from leaking outside. Heat conduction between the heat receiving portion and ring portion is prevented so the analyzer unit can be heated efficiently.

Since the hollow portion between the inner and outer tubes forms a substantially vacuum heat insulating space, the analyzer unit will not be adversely affected by the outer air temperature and can be maintained at a constant temperature.

Since the plurality of gas connection ports are radially formed, the farther from the center of the manifold, the larger the distance between the adjacent pipe connecting tools, so the pipe connecting tools can be attached and detached easily.

Since communication paths through which the corresponding gas flow paths and gas connection ports communicate with each other are formed in the respective connecting portions of the manifold, the temperatures of the communication paths can be set close to the internal temperatures of the connecting portions, and temperature fluctuation of the gas can be decreased. Also, the sectional areas of the connecting portions can be decreased to increase the heat insulating effect.

What is claimed is:

1. A gas chromatograph comprising:

a pressure resistant explosion-proof case;

heating means disposed in said pressure resistant explosion-proof case;

a heat conduction member heated by said heating means in said pressure resistant explosion-proof case and adapted to supply heat front said heating means to an outside of said pressure resistant explosion-proof case by heat conduction; and an analyzer unit disposed outside said pressure resistant explosion-proof case in contact with said heat conduction member and heated by heat supplied from said heat conduction member.

2. An apparatus according to claim 1, wherein said heat conduction member comprises:

a heat receiving portion, arranged inside the pressure resistant explosion-proof cases for receiving heat from said healing means which is arranged in the pressure resistant explosion-proof case, and said heat receiving portion has a heat supply portion facing for supplying heat conducted from said heat receiving portion to said analyze unit disposed outside said pressure resistant explosion-proof case.

3. A gas chromatograph comprising:

a pressure resistant explosion-proof case comprised of at least a housing with an opening and a manifold attached to said opening of said housing, said manifold having a plurality of gas flow paths;

art analyzer unit having a flow path selector valve and adapted to come into surface contact with an outer surface of said manifold to switch flow paths of an introduced gas, and a column for separating a component of the introduced gas;

heating means, disposed in said pressure resistant explosion-proof case, for heating an inner surface of said manifold, thereby supplying heat to said analyzer unit through said manifold; and temperature keeping means, disposed outside said pressure resistant explosion-proof case, wherein said analyzer unit is kept a constant temperature by said temperature keeping means.

4. A gas chromatograph according to claim 3, wherein said manifold comprises a heat receiving portion for receiving heat from said heating means, a ring portion with a cylindrical portion surrounding said heat receiving portion and adapted to fit in said opening of said housing, and an outer circumferential surface where said flow paths of said manifold are open, a plurality of connecting portions for connecting said ring portion and said heat receiving portion to each other, and a thermal insulator arranged between said heat receiving portion and said ring portion and adapted to block heat conduction from said heat receiving portion to said ring portion.

5. A gas chromatograph according to claim 4, wherein said heating means comprises a heater, said heat receiving portion is formed of a thick-walled cylindrical portion and a bottom plate portion to have a cup shape, and said heater is arranged in contact with an inner surface of said heat receiving portion.

6. A gas chromatograph according to claim 5, wherein said gas flow paths of said manifold are formed in said cylindrical portion of said heat receiving portion, and said ring portion has gas connection ports of said gas flow paths each with one end open in an outer circumferential surface thereof and formed radially to correspond to said connecting portions.

7. A gas chromatograph according to claim 6, wherein said connecting portions have communication paths for connecting said gas flow paths of said manifold to the other end of a corresponding one of said gas connection ports.

8. A gas chromatograph according to claim 3, wherein said temperature keeping means comprises a thermostatic chamber for accommodating said analyzer unit and keeping said analyzer at a constant temperature.

9. A gas chromatograph according to claim 8, wherein said thermostatic chamber comprises
an inner tube for accommodating said analyzer unit,
an outer tube for accommodating said inner tube, and
a substantially vacuum hollow portion formed between said inner and outer tubes.

\* \* \* \* \*